(12) United States Patent
Albright et al.

(10) Patent No.: US 7,763,267 B2
(45) Date of Patent: Jul. 27, 2010

(54) VERSATILE HIGH LOAD CONCENTRATE COMPOSITIONS FOR CONTROL OF ECTO-PARASITES

(75) Inventors: Robert B. Albright, Chalfont, PA (US); Shobhan Sabnis, Pennington, NJ (US)

(73) Assignee: Wyeth LLC, Madison, NJ (US)

(*) Notice: Subject to any disclaimer, the term of this patent is extended or adjusted under 35 U.S.C. 154(b) by 813 days.

(21) Appl. No.: 11/435,684

(22) Filed: May 17, 2006

(65) Prior Publication Data

US 2006/0269585 A1    Nov. 30, 2006

Related U.S. Application Data

(60) Provisional application No. 60/683,949, filed on May 24, 2005.

(51) Int. Cl.
*A01N 25/24* (2006.01)

(52) U.S. Cl. .......... 424/407; 424/405; 514/522

(58) Field of Classification Search .......... 514/522; 424/407, 405
See application file for complete search history.

(56) References Cited

U.S. PATENT DOCUMENTS

| | | | |
|---|---|---|---|
| 3,711,606 A * | 1/1973 | Herschler | 514/174 |
| 4,337,330 A * | 6/1982 | Robeson | 525/407 |
| 4,560,553 A | 12/1985 | Zupan | |
| 4,710,512 A | 12/1987 | Webb | |
| 5,116,850 A | 5/1992 | Stevenson | |
| 5,304,573 A | 4/1994 | Hino et al. | |
| 5,324,837 A | 6/1994 | Renga et al. | |
| 5,462,938 A | 10/1995 | Annus et al. | |
| 5,543,573 A | 8/1996 | Takagi et al. | |
| 5,708,170 A | 1/1998 | Annis et al. | |
| 5,965,137 A | 10/1999 | Petrus | |
| 5,968,990 A | 10/1999 | Jon et al. | |
| 6,110,520 A * | 8/2000 | He et al. | 426/536 |
| 6,403,063 B1 * | 6/2002 | Sawyer | 424/61 |
| 6,903,237 B2 * | 6/2005 | Yamaguchi et al. | 564/20 |
| 6,955,818 B1 | 10/2005 | Hacket et al. | |
| 2004/0122075 A1 | 6/2004 | Chiarello et al. | |

FOREIGN PATENT DOCUMENTS

| | | |
|---|---|---|
| EP | 0036138 B1 | 8/1985 |
| EP | 1413201 A | 4/2004 |
| EP | 1334661 B1 | 1/2007 |
| JP | 08268994 | 10/1996 |
| JP | 09301947 | 11/1997 |
| WO | WO 92/06076 A1 | 4/1992 |
| WO | WO 96/10560 A1 | 4/1996 |
| WO | WO 00/54591 A2 | 9/2000 |
| WO | WO 01/01781 A1 | 1/2001 |
| WO | WO 2006/002984 | 1/2006 |
| WO | WO 2006/042099 | 4/2006 |

OTHER PUBLICATIONS

Payne et al. "Structure-Activity relationships for the action of dihydropyrazole insecticides on mouse brain sodium channels", Pesticide Biochemistry and Physiology, 1998, vol. 60 pp. 177-185.

Wing et al., "A novel oxadiazine insecticide is bioactivated in lepidopteran larvae", Archives of Insect Biochemistry and Physiology, 1998, vol. 37(91) pp. 91-103.

Package Insert Frontline Top Spot® for Dogs, Merial Limited, purchased Jan. 31, 2008.

Joseph P. Remington, "Remington: The Science and Practice of Pharmacy", 19th Edition (1995), p. 1583.

* cited by examiner

*Primary Examiner*—Johann R Richter
*Assistant Examiner*—Danielle Sullivan
(74) *Attorney, Agent, or Firm*—Joel B. Silver

(57) ABSTRACT

High load concentrate compositions comprising metaflumizone, an optional bridging agent, a surfactant, and a suitable carrier solvent. These compositions may be topically administered to animals, and are useful for preventing or treating ectoparasitic infestations in warm-blooded animals for prolonged periods of time. Additionally, they may be further diluted to provide other types of formulations useable for both topical and oral administration.

20 Claims, No Drawings

VERSATILE HIGH LOAD CONCENTRATE COMPOSITIONS FOR CONTROL OF ECTOPARASITES

This application claims priority from provisional application No. 60/683,949, filed May 24, 2005, the entire disclosure of which is hereby incorporated by reference.

BACKGROUND OF THE INVENTION

Arthropod ectoparasites commonly infecting warm-blooded animals include ticks, mites, lice, fleas, blowfly, the ectoparasite *Lucilia* sp. of sheep, biting insects including keds (*Melophagus ovinus*) and migrating dipterous larvae such as *Hypoderma* sp. and *Dermataobia* in cattle, *Gastrophilus* in horses and *Cuterebra* sp. in rodents.

Metaflumizone is useful for the prevention and control of infestation by ectoparasites in warm-blooded animals. Topical administration of this active is a preferred method for administering this compound.

To provide useful protection against ectoparasitic infection or infestation in warm-blooded animals it is desirable to use formulations having a relatively high loading of active agent, but such formulations must be stable, both with respect to the physical formulation, and also, with respect to the chemical stability of the active. Metaflumizone is one of several useful insecticidal agents which have found particular application for the control of fleas and ticks on animals, particularly companion animals such as dogs, cats and horses, and livestock such as cattle, sheep and goats. It is particularly advantageous in that it can provide 4-6 weeks of protection from fleas and ticks in companion animals, but it would be potentially useful for many other species if suitable formulations could be developed. Nonetheless, formulation of metaflumizone is made difficult by its insolubility in many solvents, and its instability in the presence of primary alcohols.

It is an object of the present invention to provide a versatile composition for topical administration which comprises a relatively high loading of metaflumizone and which will provide protection from ectoparasitic infestation. Most advantageously, the formulation can function as a concentrate, which with simple modifications, can be extended to use for a wide variety of other animals. Thus, the concentrated formulation can be utilized as a small volume spot-on formulation, for instance, for protection of companion animals, while further dilutions can be utilized as conventional pour-on products for farm animals, with still further dilutions utilizable for emulsified sprays delivered through an aerosol spray or a pump spray with numerous volumes of dosage and/or application to the feed.

It is also an object of the present invention to provide a method for preventing or treating acarid or arthropod ectoparasitic infestation in animals, especially warm-blooded animals, using the compositions of the invention.

It is another object of this invention to reduce or control the proliferation of such insects in warm-blooded animals for prolonged periods of time by a topically applied active, with the formulation being mild and gentle enough to avoid adverse skin reactions upon administration, yet with the ability to be retained in the animal's skin and/or coat over the time needed for protection.

These and other objects of the present invention will become more apparent from the description thereof set forth below and the appended claims.

SUMMARY OF THE INVENTION

The present invention provides high-load concentrate compositions for topical administration which comprise on a weight to volume basis:
about 5% to about 25% of metaflumizone;
about 0% to about 15% of a bridging agent;
about 2 to about 15% of a surfactant; and
about 50% to about 80% of a carrier solvent.
The present invention further provides a method for preventing or treating ectoparasitic infection or infestation in a warm-blooded animal which method comprises topically administering to the animal an acaricidally or arthropod ectoparasiticidally effective amount of the composition of this invention.

DETAILED DESCRIPTION OF THE INVENTION

In accordance with the present invention, the high load concentrate compositions comprise metaflumizone; an optional bridging agent or penetration enhancer, a surfactant, and a carrier solvent. The invention also provides a method for preventing or treating acarid or arthropod ectoparasitic infection or infestation in warm-blooded animals by topical application of the aforesaid formulations.

Preferred high load concentrate compositions of this invention comprise on a weight to volume basis:
about 5% to about 25% of metaflumizone;
about 0% to about 15% of a bridging agent;
about 2 to about 15%, and especially about 2 to about 8%, of a surfactant and
about 50% to about 80% of a carrier solvent.
In certain embodiments about 15% to about 25% metaflumizone is included in the composition, e.g. about 20%. In certain embodiments about 5% to about 15% bridging agent is included, e.g. about 10% is included. In certain embodiments about 50% to about 60% carrier solvent is included.

While not wishing to be bound by any particular theory, it is believed that the compositions of the present invention have the requisite stability by virtue of physical and/or chemical interactions between the surfactant and the metaflumizone. The exact nature of the interactions is unknown, but apparently the surfactant stabilizes the metaflumizone in solution so as to ensure that the resultant formulation retains the desired physical characteristics over time, without loss of potency of the active. Further, the formulation is sufficiently viscous to be retained upon or in the animal's skin and/or hair, and be released over the desired period of time.

Uniquely, it has been found these high load concentrate compositions can be further utilized to prepare more dilute compositions for application in various other manners, i.e., for use as a pour-on for large animals, as a spray for large animals or for outdoor use, and as a water-dilutable formulation for addition to the feed and/or water supply of animals under treatment. This has the dual advantage of providing a concentrated formulation that can be shipped to the end-user for dilution and use, or to an intermediate formulator to prepare the compositions. The high loading of metaflumizone in the formulation thus provides a small volume of formulation to use as a "spot-on" formulation, for instance, for companion animals, especially felines. The concentrate can then be diluted by an appropriate organic solvent for use as a pour-on or in a spray, or with water, to provide the feed/water additive.

Metaflumizone, as well as its use in veterinary applications, is described in U.S. Pat. No. 5,543,573, and U.S. Published Application 2004-0122075A1, both incorporated herein by reference. Chemically, it is known as (E Z)-2-[2-(4-cyanophenyl)-1-[3-(trifluoromethyl)phenyl]ethylidene]-N-[4-(trifluoromethoxy)phenyl]hydrazinecarboxamide.

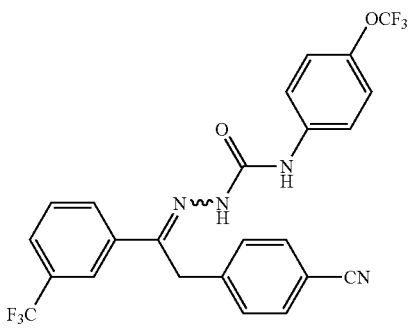

Bridging agents or penetration enhancers suitable for use in the compositions of this invention include, but are not limited to, alkyl methyl sulfoxides (such as dimethyl sulfoxide, decylmethyl sulfoxide and tetradecylmethyl sulfoxide); pyrrolidones (such as 2-pyrrolidone, N-methyl-2-pyrrolidone and N-(2-hydroxyethyl) pyrrolidone); laurocapram; and miscellaneous solvents such as acetone, dimethyl acetamide, dimethyl formamide, and tetrahydrofurfuryl alcohol. Other bridging agents include amphiphiles such as L-amino acids, and fatty acids. Additional bridging agents are disclosed in *Remington: The Science and Practice of Pharmacy*, 19$^{th}$ Edition (1995) on page 1583. Typically, the bridging agents is used at a level of about 10% w/v of the formulation where the end use is for a topical application, but this may vary, especially when the end use of the composition is for oral administration.

The surfactant utilized in the present invention may be a single surfactant, or a mixture of two or more surfactants, again, in part dependent upon whether the end use of the composition is topical or oral. The surfactant should be non-irritating, and non-toxic. Preferred are non-ionic, low foaming surfactants, such as the alcohol alkoxylate surfactants, with those sold by Uniqema under the tradename Synperonic® NCA 810, 830 and 850 being especially suitable. Other useful surfactants are the nonylphenol ethoxylates, with those sold under the tradename Tergitol® NP by the Dow Chemical Company being preferred. Additional surfactants, including appropriately chosen anionic and cationic surfactants, can also be utilized in the formulations of the present invention. Especially useful properties are found in anionic surfactants, such as dioctylsulfosuccinate salts.

Typically, the surfactant is utilized at a level of about 2 to about 15% w/v, especially about 2 to about 8% w/v, of the composition, but this may vary somewhat depending upon the end use of the composition. In the case where the end use of the concentrate is as a spray formulation, or as a water-dispersible feed/water additive, it may be desirable to add a further surfactant to ensure that the diluted formulation will be a unitary phase. This ensures that the spray will not block the spray nozzle, and that the active will be dispersed equally throughout the diluted product. In such cases, the additional surfactant may be added to the concentrate formulation, or added to the end use formulation with the diluting solvent. Particularly useful surfactants for use with an organic solvent diluent are non-ionic surfactants such as polyoxyl 35 castor oil sold under the Cremophore® tradename.

The carrier solvent for the compositions of the present invention may be a single solvent, or a mixture of solvents. Due to the instability of metaflumizone in the presence of primary alcohols, preferred solvents are non-hydroxyl-group-containing solvents, especially those such as γ-hexalactone (also known as γ-caprolactone; ethyl butyrolactone; γ-ethyl-n-butyrolactone; hexanolide-1,4; 4-hydroxy hexanoic acid γ-lactone or tonkalide). Optionally, other such solvents such as N,N-diethyl-m-toluamide, eucalyptol, dimethyl isosorbide, diisopropyl adipate and/or 1-methoxy-2-propyl acetate can be utilized in combination with the γ-hexalactone to comprise the carrier solvent.

To manufacture the high load concentrate composition of the present invention, the metaflumizone is dissolved in the carrier solvent or solvents, and the surfactant and bridging agent, if desired added to the mixture. This composition can then be utilized as a high load spot-on, or further diluted for additional uses.

An especially preferred composition for topical administration to warm-blooded animals comprises, on a weight to volume basis, about 5% to about 25% metaflumizone; about 10% of a bridging agent, especially dimethyl sulfoxide, about 2-about 8% of a non-ionic, low foam surfactant; and about 50-60% carrier solvent, especially γ-hexalactone.

The high load concentrate compositions of this invention may further comprise other agents known in the art, such as preservatives (e.g., methylparaben and propylparaben), colorants, antioxidants, and the like. Generally, these agents would be present in the compositions in an amount up to about 2% on a weight to volume basis.

When topically administered, the compositions of this invention are highly effective for preventing or treating ecto-parasitic infection and infestation for prolonged periods of time in warm-blooded animals such as cows, sheep, horses, camels, deer, swine, goats, dogs, cats, birds, and the like. Representative dosages for application to companions are, for instance, 20 mg/kg for dogs, and 40 mg/kg for cats, but lower dosages down to 5 mg/kg show efficacy on large animals such as horses and cattle.

In order to facilitate a further understanding of the invention, the following examples are presented primarily for the purpose of illustrating specific embodiments thereof. The invention is not to be deemed limited thereby, except as defined in the claims.

EXAMPLE 1

Preparation of Metaflumizone High Load Concentrate, Suitable for Use as a Spot-on To 10 grams of DMSO is added to 40 grams of γ-hexalactone. To this solvent mixture is added 20 g. of metaflumizone. Mild heat (40° C.) may be used to facilitate the process of dissolution. To the resulting solution, 6 grams of Synperonic® NCA 830 brand of alcohol alkoxylate surfactant is added with stirring. Bring to 100 ml with γ-hexalactone.

Thus formulated, the composition can be applied as a "spot-on" (topical small dose) treatment for cats.

The efficacy of such a formulation is given in the efficacy table below:

|  | Days after treatment | | | |
| --- | --- | --- | --- | --- |
|  | 2 | 15 | 29 | 57 |
| Untreated Control group, number of fleas/cat | 53.9 | 83.9 | 62.9 | 65.2 |
| 20% metaflumizone spot-on 40 mg/kg % Efficacy | 100.0 | 100.0 | 100.0 | 97.1 |

EXAMPLE 2

Preparation of Metaflumizone Pour-on from High Load Concentrate of Example 1

To 25 ml of the high load concentrate prepared in Example 1 is added q.s. 100 ml γ-hexalactone. This provides a pour-on formulation having sufficient metaflumizone and volume to treat 5 head of cattle weighing 200 Kg each at 5 mg/kg dose rate.

EXAMPLE 3

Preparation of High Load Concentrate for Use as a Concentrate to Prepare Metaflumizone Spray or Feed/Water Supplement 12.59 grams of metaflumizone is added to dimethyl isosorbide using mild heating (approximately 40° C.). To this solution is added 109.92 grams Cremophor® EL (polyethoxylated castor oil, sold by Basf Aktiengesellschaft), with stirring, followed by q.s. 200 ml 1-methoxy-2-propyl acetate The resultant solution is stored until ready for use, whereupon it can be diluted with water for use as a spray (17 ml of concentrate diluted to 3500 ml with water), or with water for use as a feed/water additive (in approximately the same ratio).

This formulation was diluted with water to a metaflumizone concentration of 10 mg/kg bodyweight, and applied to sheep at 1500 ml/animal to test the effect of metaflumizone on biting lice

|  | Days after treatment | | | |
| --- | --- | --- | --- | --- |
|  | 7 | 14 | 21 | 28 |
| Untreated Control group, number of lice/animal | 140.2 | 293.2 | 542.2 | 824.8 |
| 10 mg/kg metaflumizone dosed as a body spray % Efficacy | 100 | 100 | 100 | 100 |

EXAMPLE 4

Preparation of Spot-on Formulations Using Various Surfactant Chemistries and Solvent Systems, % w/v

| Ingredient | Formulation 5 | Formulation 6 | Formulation 7 | Formulation 8 |
| --- | --- | --- | --- | --- |
| Metaflumizone | 25 | 25 | 25 | 25 |
| DMSO | 35 | 0 | 0 | 0 |
| Tergitol ® NP13 | 5 | 5 | 0 | 10 |
| Synperonic ® NCA 830 | 0 | 0 | 0 | 0 |
| Aerosol OT ® (dioctyl sodium sulfosuccinate) | 0 | 0 | 12.5 | 0 |
| ethanol | 0 | 0 | 0 | 10 |
| Ethylene glycol propylene ether | 0 | 35 | 0 | 0 |
| γ-hexalactone | q.s | q.s. | q.s. | q.s. |

|  | Formulation 9 | Formulation 10 | Formulation 11 | Formulation 12 |
| --- | --- | --- | --- | --- |
| Metaflumizone | 20 | 20 | 20 | 20 |
| Tergitol ® NP13 | 0 | 0 | 0 | 5 |
| N,N-Diethyltoluamide | 10 | 10 | 10 | 0 |
| Cineole | 10 | 10 | 10 | 0 |
| DMSO | 0 | 0 | 0 | 10 |
| Crodamol ® PMP (polyoxypropylene (2) myristyl ether propionate) | 0 | 1 | 0 | 0 |

-continued

| Ingredient | | | | |
|---|---|---|---|---|
| Isopropyl myristate | 0 | 0 | 1 | 0 |
| γ-hexalactone | q.s | q.s. | q.s | q.s. |

What is claimed is:

1. A composition for topical administration which comprises on a weight to volume basis:
   about 5% to about 25% of metaflumizone;
   about 2% to about 15% of a surfactant selected from an alcohol alkoxylate surfactant, nonylphenol ethoxylate surfactant or polyoxyl 35 castor oil surfactant; and
   about 50% to 80% of a carrier solvent.

2. The composition according to claim 1, which comprises about 15% to 25% metaflumizone.

3. The composition according to claim 1 wherein the surfactant is an alcohol alkoxylate surfactant.

4. The composition according to claim 2 wherein the surfactant is a nonylphenol ethoxylate surfactant.

5. The composition according to claim 1 wherein the surfactant is present at a level of about 2% to about 8% w/v.

6. The composition according to claim 2 wherein the surfactant is present at a level of about 2% to about 8% w/v.

7. The composition according to claim 1 wherein the composition further comprises a bridging agent.

8. The composition according to claim 7 wherein the bridging agent is dimethyl sulfoxide.

9. The composition according to claim 1 wherein the carrier solvent is γ-hexylactone.

10. The composition according to claim 2 wherein the carrier solvent is γ-hexalactone.

11. The composition according to claim 1 wherein the carrier solvent is 1-methoxy-2-propyl acetate.

12. The composition according to claim 1 which additionally contains up to 2% of one or more preservatives, colorants, antioxidants, or stabilizers.

13. A method for preventing or treating ectoparasitic infection or infestation in a warm-blooded animal which method comprises topically administering to the animal effective amount of a composition according to claim 1.

14. The method according to claim 13 wherein the animal is selected from the group consisting of a cow, a sheep, a horse, a camel, a deer, a swine, a goat, a dog, a cat, and a bird.

15. The method according to claim 13 wherein the composition comprises about 5% to about 25% metaflumizone; about 10% of a bridging agent; about 2% to about 8% surfactant; and about 50% to about 60% carrier solvent.

16. The method according to claim 13 wherein the composition comprises γ-hexylactone as the carrier solvent.

17. The method according to claim 13 wherein the composition is further diluted for use as a pour-on composition.

18. The method according to claim 16 wherein the composition further comprises 1-methoxy-2-propyl acetate.

19. The method according to claim 13 wherein the composition is further diluted for use as a spray or feed/water additive.

20. A method for preventing or treating ectoparasitic infection or infestation in a warm-blooded animal which method comprises topically administering to the animal an effective amount of a pour-on composition, comprising: the composition according to claim 1; and a diluent.

* * * * *